(12) United States Patent
Faigl et al.

(10) Patent No.: US 11,091,436 B2
(45) Date of Patent: Aug. 17, 2021

(54) PROCESS FOR THE SEPARATION OF OPTICAL ISOMERS OF RACEMIC 3-ALKYLPIPERIDINE-CARBOXYLIC ACID ETHYL ESTERS

(71) Applicant: RICHTER GEDEON NYRT., Budapest (HU)

(72) Inventors: Ferenc Faigl, Budapest (HU); Béla Mátravölgyi, Budapest (HU); Ágnes Mizsák, Budapest (HU)

(73) Assignee: RICHTER GEDEON NYRT., Budapest (HU)

( * ) Notice: Subject to any disclaimer, the term of this patent is extended or adjusted under 35 U.S.C. 154(b) by 0 days.

(21) Appl. No.: 16/493,449

(22) PCT Filed: Mar. 12, 2018

(86) PCT No.: PCT/IB2018/051600
§ 371 (c)(1),
(2) Date: Sep. 12, 2019

(87) PCT Pub. No.: WO2018/167631
PCT Pub. Date: Sep. 20, 2018

(65) Prior Publication Data
US 2020/0131126 A1    Apr. 30, 2020

(30) Foreign Application Priority Data
Mar. 13, 2017    (HU) .................................. P1700109

(51) Int. Cl.
| | | |
|---|---|---|
| *C07D 211/60* | (2006.01) | |
| *B01D 9/00* | (2006.01) | |
| *C07B 57/00* | (2006.01) | |
| *C07B 63/04* | (2006.01) | |

(52) U.S. Cl.
CPC ............ *C07D 211/60* (2013.01); *B01D 9/005* (2013.01); *C07B 57/00* (2013.01); *C07B 63/04* (2013.01); *C07B 2200/07* (2013.01)

(58) Field of Classification Search
CPC .................................................. C07D 211/60
USPC ........................................................ 546/245
See application file for complete search history.

(56) References Cited

U.S. PATENT DOCUMENTS

| | | |
|---|---|---|
| 3,904,632 A | 9/1975 | Hollander et al. |
| 5,492,916 A | 2/1996 | Morriello et al. |
| 5,721,250 A | 2/1998 | Morriello et al. |
| 6,362,188 B1 | 3/2002 | Guzi et al. |

FOREIGN PATENT DOCUMENTS

| | | |
|---|---|---|
| WO | WO 95/13069 | 5/1995 |
| WO | WO 00/37458 | 6/2000 |
| WO | WO 00/56727 | 9/2000 |
| WO | WO 2008/117982 | 10/2008 |
| WO | WO 2009/099086 | 8/2009 |

OTHER PUBLICATIONS

Báthori, N.B., et al., "One hydrogen bond does not a separation make, or does it? Resolution of amines by diacetoneketogulonic acid," *Chem. Commun.* 51:5664-5667, 2015, The Royal Society of Chemistry, United Kingdom.
Bettoni, G., et al.,"Absolute configuration and optical purity of 3-substituted piperidines," *Gazzetta Chimica Italiana* 102:189-195, 1972, Societá Chimica Italiana, Italy.
Bjorge, S., et al., "Synthesis and Metabolic Profile of CI-966: A Potent, Orally-Active Inhibitor of GABA Update," *Drug Dev. Res.* 21:189-193, 1990, John Wiley & Sons Inc., United States.
Fitzi, R., et al., "Resolution and use in α-amino acid synthesis of imidazolidinone glycine derivatives," *Tetrahedron* 44(17):5277-5292, 1988, Pergamon Press PLC, United Kingdom.
Magnus, P., et al., "Synthesis of the Vinblastine-like Antitumor Bis-Indole Alkaloid Navelbine Analogue Desethyldihydronavelbine," *J. Org. Chem.* 56(3):1166-1170, 1991, The American Chemical Society, United States.
Pettersson, C., et al., "Chiral Separation of Amines Using Reversed-Phased Ion-Pair Chromatography," *Chirality* 5:241-245, 1993, Wiley-Liss, Inc., United States.
Trstenjak, U., et al., "Transformation of a selective factor Xa inhibitor rivaroxaban into a dual factor Xa/thrombin inhibitor by modification of the morpholin-3-one moiety," *Med. Chem. Commun.* 5:197-202, 2014, Royal Society of Chemistry, United Kingdom.
Yang, L., et al., "1-[2(R)-(2-Amino-2-methylpropionyl-amino)-3-(1H-indol-3-yl)propionyl]-3-benzylpiperidine-3(S)-carboxylic Acid Ethyl Ester (L-163,540): A Potent, Orally Bioavailable, and Short-Duration Growth Hormone Secretagogue," *J. Med. Chem.* 41(14):2439-2441, 1998, The American Chemical Society, United States.
Zorn, S.H., et al., "(R)-Nipecotic Acid Ethyl Ester: A Direct-Acting Cholinergic Agonist that Displays Greater Efficacy at $M_2$ than at $M_1$ Muscarinic Receptors," *J. Pharmacol. Exp. Therap.* 242(1):173-178, 1987, The American Society for Pharmacology and Experimental Therapeutics, United States.

*Primary Examiner* — Patricia L Morris
(74) *Attorney, Agent, or Firm* — Sterne, Kessler, Goldstein & Fox P.L.L.C.

(57) ABSTRACT

The subject-matter of the invention is process for the separation of optical isomers of racemic 3-alk-3-carboxylic acid ethyl esters of formula rac-I with the resolving agent (II) (−)-2,3:4,5-di-O-izopropylidene-2-keto-L-gulonic acid (hereinafter: diacetone-L-ketogulonic acid).

16 Claims, 1 Drawing Sheet

PROCESS FOR THE SEPARATION OF OPTICAL ISOMERS OF RACEMIC 3-ALKYLPIPERIDINE-CARBOXYLIC ACID ETHYL ESTERS

FIELD OF THE INVENTION

Figure 1:
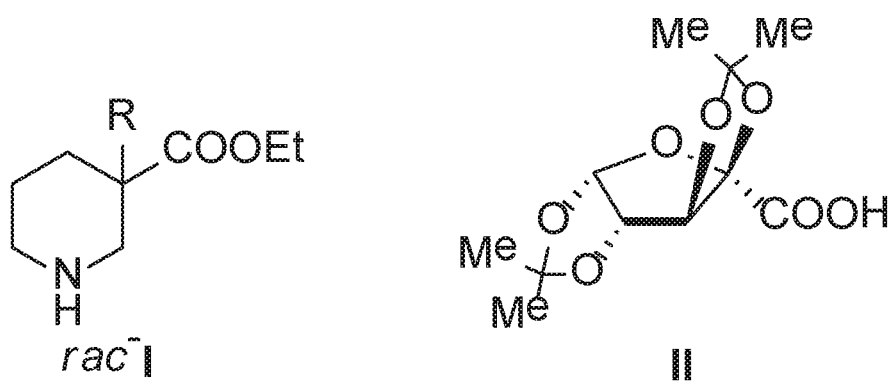

The subject-matter of the invention is process for the separation of optical isomers of racemic 3-alkylpiperidine-3-carboxylic acid ethyl esters of formula (rac-I) with the resolving agent (II) (−)-2,3:4,5-di-O-izopropylidene-2-keto-L-gulonic acid (hereinafter: diacetone-L-ketogulonic acid). Formulae of the racemic compounds and the resolving agent can be seen on FIG. 1 wherein in the formula of rac-I R means C1-C3 carbon chain length normal or branched alkyl group, especially methyl-(rac-Ia, R=Me), ethyl-(rac-Ib, R=Et) or isopropyl group (rac-Ic, R=iPr).

BACKGROUND OF THE INVENTION

The parent compound not having alkyl substituent at C3-position, the nipecotic acid ethyl ester (rac-Id, R=H) and its optical isomers are widely used intermediates in the synthesis of compounds having therapeautic effect. This structural unit is contained in for example different dual acting Xa factor/thrombin inhibitor compounds (U. Trstenjak, J. Ilas, D. Kikelj: *Med. Chem. Commun.*, 2014, 5, 197-202), cholinergic agonists (S. H. Zorn, R. S. Duman, A. Giachetti, R. Micheletti, E. Giraldo, P. Krogsgaard-Larsen, S. J. Enna: *Journal of Pharmacology and Experimental Therapeutics*, 1987, 242(1), 173-178), inhibitors of GABA uptake (s. Bjorge, A. Black, H. Bockbrader, T. Chang, V. E. Gregor, S. J. Lobbestael, D. Nugiel, M. R. Pavia, L. Radulovic, T. Woolf: *Drug Development Research*, 1990, 21(3), 189-193).

Racemic nipecotic acid ethyl ester derivatives containing methyl-(rac-Ia, R=Me) (for example: T. Guzi, D. F. Rane, A. K. Mallams, A. B. Cooper, R. J. Doll, V. M. Girijavallabhan, A. G. Taveras, C. Strickland, J. M. Kelly, J. Chao: U.S. Pat. No. 6,362,188 (Mar. 26, 2002) patent, T. Guzi, D. F. Rane, A. K. Mallams, A. B. Cooper, R. J. Doll, V. M. Girijavallabhan, A. G. Taveras, C. Strickland, J. M. Kelly, J. Chao: PCT Int. Appl. (2000), WO 2000037458 A1 (Jun. 29, 2000) patent application), ethyl-(rac-Ib, R=Et) (Guzi, D. F. Rane, A. K. Mallams, A. B. Cooper, R. J. Doll, V. M. Girijavallabhan, A. G. Taveras, C. Strickland, J. M. Kelly, J. Chao: PCT Int. Appl. (2000), WO 2000037458 A1 (Jun. 29, 2000) patent application, G. J. Morriello, A. A. Patchett, L. Yang: U.S. Pat. No. 5,492,916 A (Feb. 20, 1996), G. J. Morriello, L. Yang, A. A. Patchett: U.S. Pat. No. 5,721,250 A (Feb. 24, 1998), G. J. Morriello, A. A. Patchett, L. Yang M. H. Chen, R. Nargund: WO 199513069 A1 (May 18, 1995), T. Nagase, T. Sasaki, T. Takahashi: WO 2009099086 A1 (Aug. 13, 2009) patent applications), benzyl group, respectively (rac-Ic, R=Bn) (J. M. Cho, S. Ro, D. Shin, Y.-L. Hyun, J. H. Lee, G. H. Yon, E. B. Choi, H. K. Lee, C. S. Pak, H. G. Cheon, S. D. Rhee, W. H. Jung, H. C. Yang, S. H. Jo, E. Lee, J. H. Im: WO 2008117982 A1 (Oct. 2, 2008) patent application), at C3-position are also known in the art.

The racemic n-propyl and n-butil (rac-If, R=Pr; rac-Ig, R=Bu) derivatives are likewise disclosed as intermediates of growth hormone releasing compounds (G. J. Morriello, L. Yang, A. A. Patchett: U.S. Pat. No. 5,721,250 A (Feb. 24, 1998) patent G. J. Morriello, A. A. Patchett, L. Yang, M. H. Cheng, R. Nargund: WO 95/13069 (May 18, 1995) patent application). However, no data can be found about the racemic 3-isopropyl derivative (rac-Ic, R=i-Pr) in the art.

The biological effect of the mirror image pairs of the nipecotic acid ethyl ester and the 3-alkyl derivatives possessing chirality center at C3-position may be extremely different, hence the efficient separation of optical isomers is of great practical importance. Bettoni et al. described firstly the separation of optical isomers of the racemic nipecotic acid ethyl ester (rac-Id) (G. Bettoni, E. Duranti, V. Tortorella: *Gazz. Chim. Ital.*, 1972, 102, 189). The racemic ester was dissolved warmly in five volumes of 95% ethanol, equivalent amount of natural (R,R)-tartaric acid was added, then the diastereomeric salt crystallyzing during cooling, after its filtration, was recrystallized from 95% ethanol and the pure diastereomeric salt was obtained in 56% yield based on the half of the racemic material. The optically active base was liberated from the salt by sodium hydroxide in the form of colorless oil. Magnus et al. (P. Magnus, L. S. Thurston, *J. Org. Chem.*, 1991, 56, 1166-1170) and co-workers of the Schering company in 2002 applied this same process for the preparation of new inhibitors of farnesyl protein transferase (FPT) enzyme (T. Guzi, D. F. Rane, A. K. Mallams, A. B. Cooper, R. J. Doll, V. M. Girijavallabhan, A. G. Taveras, C. Strickland, J. M. Kelly, J. Chao: U.S. Pat. No. 6,362,188 (Mar. 26, 2002) patent).

Several procedures have been described for the resolution of the rac-Ia (R=Me) ester. According to one of the methods (T. Guzi, D. F. Rane, A. K. Mallams, A. B. Cooper, R. J. Doll, V. M. Girijavallabhan, A. G. Taveras, C. Strickland, J. M. Kelly, J. Chao: U.S. Pat. No. 6,362,188 (Mar. 26, 2002) patent, T. Guzi, D. F. Rane, A. K. Mallams, A. B. Cooper, R. J. Doll, V. M. Girijavallabhan, A. G. Taveras, C. Strickland, J. M. Kelly, J. Chao: PCT Int. Appl. (2000), WO 2000037458 A1 (Jun. 29, 2000) patent application) the resolution of rac-Ia was carried out with the non-natural (−)-(S,S)-tartaric acid in acetone/water solvent mixture, thus the (S)-Ia enantiomer was obtained in 18% yield from the crystallized diastereomeric salt.

The significant disadvantage of the process was that the non-naturally occuring and thus remarkably more expensive (−)-(S,S)-tartaric acid had to be used in the preparation of useful Ia enantiomer for the inventors. In another procedure (S. N. Owen, E. M. Seward, C. J. Swain, B. J. Williams: WO 0056727 (Sep. 28, 2000) patent application) the preparation of the diastereomeric salt was carried out with a quarter mol O,O'-dibenzoyl-D-tartaric acid based on the racemic base which crystallized from the mixture of ethyl acetate/isopropanol=1/4. The (+)-(R)-Ia isomer was obtained in 25% yield from the salt based on the half of the racemic base. The resolution was also achieved with O,O'-di-p-toluoyl-D-tartaric acid in ethyl acetate (S. N. Owen, E. M. Seward, C. J. Swain, B. J. Williams: WO 200056727 (Sep. 28, 2000) patent application).

The diastereomeric salt containing the (R)-Ia enantiomer was obtained in 56% yield based on the half of the racemic base from the reaction mixture and the preparation of the (R)-Ia HCl salt was also described. The disadvantage of the mentioned resolution methods is that they could obtain the diastereomeric salt in only small or medium yield and they do not provide a solution for preparing the enantiomer remaining in the filtrate in its pure form.

The resolution of the racemic 3-benzylpiperidine-3-carboxylic acid ethyl ester (rac-Ie) was described in an article (L. Yang, G. Morriello, A. A. Patchett, K. Leung, T. Jacks, K. Cheng, K. D. Schleim, W. Feeney, W. W.-S. Chan, Sh-H. L. Chiu, R. G. Smith: *J. Med. Chem.* 1998, 41, 2439-2441. L. Yang, G. Morriello, A. A. Patchett, K. Leung, T. Jacks, K. Cheng, K. D. Schleim, W. Feeney, W. W.-S. Chan, Sh-H. L. Chiu, R. G. Smith: *J. Med. Chem.* 1998, 41, 2439-2441.)

with (R,R)-tartaric acid in the mixture of acetone/water=4/1. According to the article the (S)-Ie base was obtained from the crystallized diastereomeric salt.

There is however no known method for the resolution of rac-Ib, rac-Ic and rac-If,g esters and based on the testimony of art the pure enantiomers of these compounds have so far not been prepared by other (eg. asymmetric synthesis) methods.

We therefore found when studying the literature that among the 3-alkylnipecotic acid ethyl esters only processes for the separation of optical isomers of rac-Ia can be found which have the disadvantage of their low efficiency and the use of expensive non-natural tartaric acid or its derivatives as resolving agent and that no solution is provided for recovering the enantiomer residing in the filtrate in pure form. So far no resolution or enantioselective production method have been described for the preparation of enantiomers of the compounds Ib-g.

Considering the disadvantages of the known procedures for the resolution of the rac-Ia and that no available process in the art for the separation of enantioniers of Ib,c esters, our aim was to elaborate an industrial-scale method for the production of high enantiomeric purity (+)-Ia-c and (−)-Ia-c by diastereomeric salt formation resultion of the racemic ester. We aimed to develop a method which does not contain technological steps that require difficult and extreme circumstences, and that the products using simple operations, with adequate purity, can be isolated by high efficiency.

During our experiment we have unexpetedly, surprisingly found that the rac-Ia compounds reacted with the diacetone-L-ketogulonic acid of formula II which was never used in their resolution in a suitable solvent form well-crystallizing diastereomeric salt, which salts contain high enantiomeric purity (R)-Ia, (R)-Ib or (S)-Ic isomers and can be obtained in high yields.

We also unexpectedly observed that the (S)-Ia, (S)-Ib or (R)-Ic enantiomers from the filtrate of the diastereomeric salt formation with simple processing operations, for example in the form of hydrochloride salts can also be obtained with high enantiomeric purity and the nearly racemic composition Ia-c compounds remaining in solution can be recycled to the diastereomeric salt forming process. That is, by the processing of the filtration of the salt formation that we developed we unpredictably achieved such a sharp separation that besides the precipitated crystalline hydrochloride salt of the pure Ia-c enantiomers there remain small amount but practically racemic composition of Ia-c in the solution which can thus be recycled without loss in the first diastereomeric salt-forming step of the resolution process.

We have also noticed that from crystalline diastereomeric salts obtained by resolution, if desired, by recrystallizing once the salts containing the appropriate Ia-c enantiomers in completely pure form can be obtained, the substance remaining in the filtrate of the recrystallization can be recycled to the resolution process. Considering therefore the recirculation of racemic proportions both enantiomers of the racemic compounds Ia-c can be prepared in ee>98% purity, with excellent efficiency (>93% yield).

The great advantage of the process is that with the same resolving agent all three racemates (rac-Ia-c) be divided to their ena.ntiotners with excellent efficiency. A preparation of diastereomeric salts is cheap, and can be carried out in low-toxic solvents used in the pharmaceutical industry under mild conditions. The recirculation of rac-Ia-c recovered from the salt recrystallization and processing of the salt-forming filtrates not only increases the efficiency of the resolution process but also significantly reduces the environmental burden.

The (R)-Ia.II, (R)-Ib.II, és (S)-Ic.II salts produced by us are novel which are not yet know in the art. Also novel compounds are the (S)-Ib.HCl, (R)-Ic.HCl salts and the mirror image pairs thereof, the enantiomers of formulae (R)-Ib, (S)-Ib, (R)-Ic and (S)-Ic which can be released therefrom in a manner known per se, respectively.

The absolute configuartion of the Ia enantiomers is known in the art. Based on this, it has been found that when the rac-Ia is resolved the (R)-I enantiomer is enriched in the crystalline diastereomeric salt formed with II, the (S)-Ia isomer remains in the filtrate. The absolute configuration of the Ib and Ic enantiomers that we firstly prepared was determined by single crystal X-ray diffraction. Accordingly, the crystalline diastereomers contain the diastereomeric salt compositions of (R)-Ib.II and (S)-Ic.II.

DETAILED DESCRIPTION OF THE INVENTION

Figure 2:
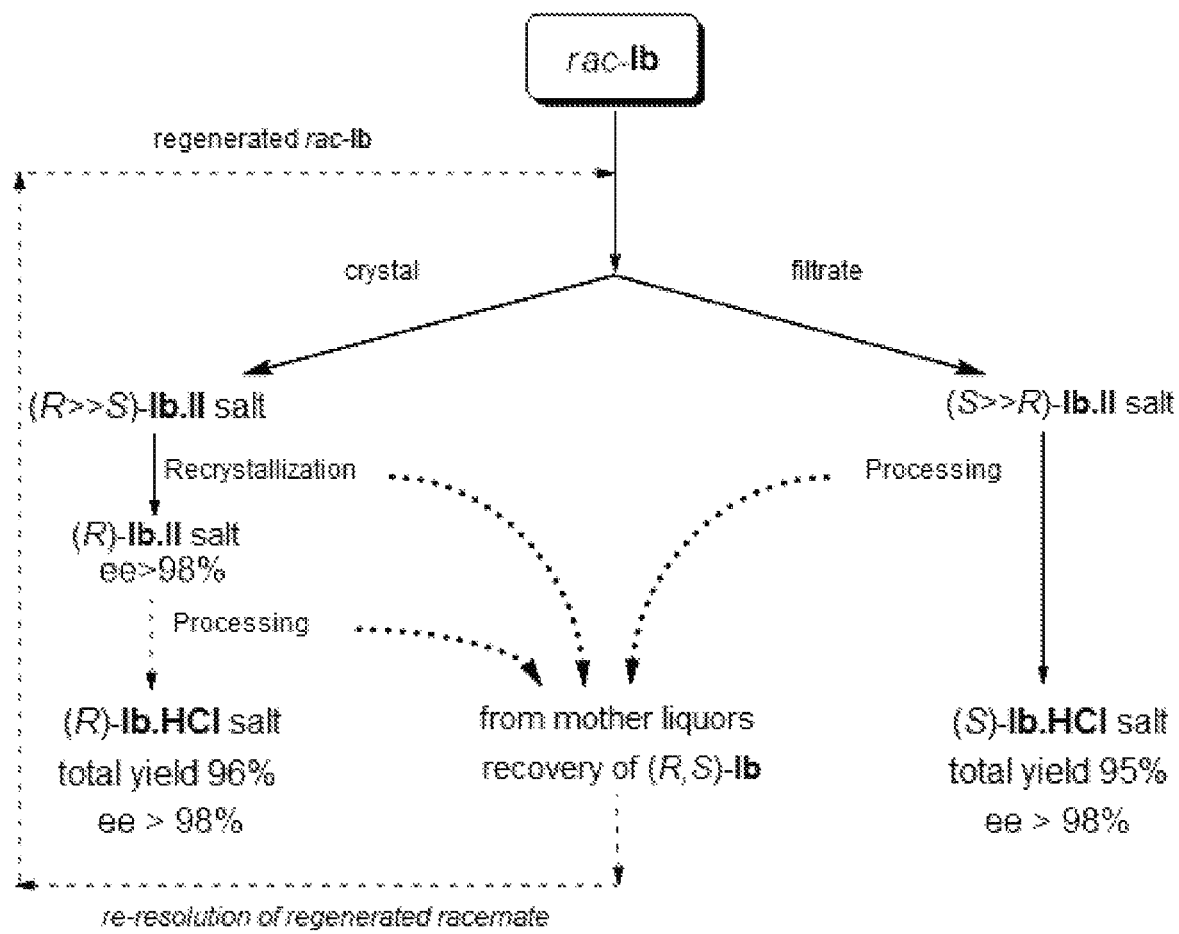

The process of the present invention is carried out by the racemic bases Ia or Ib or Ic prepared by one of the methods known in the art, which are preferably freshly liberated, for example from hydrochloric acid salts, are separately dissolved warmly in acetone, then the resolving agent II is added in an amount of 0.8 to 1.2 equivalents based on the amount of the racemic base, preferably 1 equivalent, and then to the boiling solution under stirring the appropriate diastereomer seed crystal is added, if necessary, and allowing the mixture to cool to room temperature. The crystalline diastereomeric salt, depending on the starting racemate containing either the (R)-Ia.II or the (R)-Ib.II or the (S)-Ic.II diastereomer in excess, is separated by filtration and the (R)-Ia, (R)-Ib or (S)-Ic bases are obtained therefrom by extraction after alkaline aqueous stirring. Alternatively, if desired, the crystalline diastereomeric salts prior to processing can be recrystallized from a suitable solvent, for example acetone or isopropanol and then processed. The combined filtrates of the diastereomeric salt formation and optional recrystallization are evaporated, the (S>R)-Ia, (S>R)-Ib or (R>S)-Ic bases are recovered from the residue by extraction after alkaline aqueous stirring and after evaporating the organic solvent, the evaporation residue bases are dissolved in ethyl acetate hydrochloric acid solution, then the solution is cooled and the crystallizing (S)-Ia.HCl, (S)-Ib.HCl or (R)-Ic.HCl salts of high enantiomeric purity were filtered off, the filtrate is evaporated and the bases are recovered from the residue of nearly racemic composition of (R,S)-Ia.HCl, (R,S)-Ib.HCl or (R,S)-Ic.HCl salts by extraction after alkaline aqueous stirring and recycled to the diastereomeric salt formation process. The process of the present invention is illustrated by way of an example of rac-Ib resolving processes in FIG. 2 without limiting the implementation of our method to a kind of sequence of operations shown in the flow chart.

The advantages of our invention are summarized below:

A novel, non-known process was developed for the diastereomeric salt-forming separation of optical isomers of rac-Ia-c amines of great importance in the pharmaceutical point of view, in which diastereomeric salts formed with the resolving agent prepared from natural raw material, available in high volume can be efficiently recovered by a simple crystallization process and purified according to their excellent crystallization tendency, and thus, in the case of rac-Ia high chemical and optical purity enantiomers of Ia can be prepared economically, in an easier way than in the method known in the art, our process developed for the separation of the optical isomers of rac-Ib and rac-Ic is the first and extremely efficient and scalable resolution method according to the scientific literature.

Another advantage of our process, that solvents suitable for the formation and recrystallization of diastereomeric salt and the processing steps are cheap and well regenerable, meet the criteria for modern pharmaceutical production methods are used, furthermore, the efficiency of resolution is less sensitive for the change in the salt-forming parameters, the process is robust, suitable for industrial scale.

Still an advantage of the process of our invention is that in the resolution process the preparation of both pure Ia, Ib or Ic enantiomers is simple, can be carried out by enantiomer enrichment steps built into the processing operations, and residual racemic fractions can be recycled to the beginning of the resolution process providing the decomposition of the total amount of racemic substance to pure enantiomers.

The diastereomeric salts produced by our process are novel, stable compounds which can be directly used in the synthesis of pharmaceutically active substances, or optionally the hydrochloride salt of the Ia-c amines or the free amines can be liberated by simple chemical and separation operations thereof.

In summary, we developed such novel process which is suitable for the economic and industrial scale preparation of the Ia-c enantiomers starting from rac-Ia-c amines. The purity of Ia-c enantiomers obtained by our process meet the increasingly stringent quality requirements for pharmaceutical intermediates.

The process of the invention is illustrated by the following embodiments without limiting the subject-matter of the invention.

EXAMPLES

1. The Resolution of 3-methylpiperidine-3-carboxylic acid ethyl ester (rac-Ia)

The rac-Ia amine (13.9 g, 80.0 mmol) was dissolved in 140 ml of acetone and a small amount of (R)-Ia.II seed crystals (about 0.05 g) were added to the warm solution, then the diacetone-L-ketogulonic acid monohydrate (II, 23.9 g, 80.8 mmol) was added while stirring and the reaction mixture was allowed to cool slowly. The resulting suspension was heated to boil under reflux cooling after half an hour, and allowed again to cool slowly after half an hour of stirring. The crystal suspension was stirred overnight at room temperature, then filtered off, washed with acetone (3×15 mL), dried. The nutsche wet cake (about 27.5 g) was dried at room temperature (dry weight 18.4 g). The dry salt was dissolved in hot isopropanol (404 mL) and allowed to cool at room temperature while stirring, stirred for further two hours, filtered, washed on the filter with isopropanol. The recrystallized dry (R)-Ia.II diastereomeric salt weighted 15.2 g, 83%, (R)-Ia enantiomeric excess, ee: 98.5% (HPLC), Mp: 188° C. (decomp.)

If necessary, the diastereomeric salt can be processed in the same way as the evaporation residue obtained from the filtrate of the salt formation (see the following paragraph). The enantiomeric purity of the so-produced (R)-Ia.HCl is 98.5%, Mp: 138-140° C., $[\alpha]_D$: −5.3 (c: 1, CHCl$_3$).

It should be noted that in the disclosure of WO 00/56727 (application number PCT(GB00)000974) [11] (Merck) the rotation of (R)-1 base was given as $[\alpha]_D$+9.0 (c: 1, MeOH), while the specific rotation of the (R)-1.HCl salt prepared from the base is of opposite sign to the free base according to the patent, $[\alpha]_D$−5.0 (c: 1, MeOH), and the hydrochloric acid salt was obtained from ethyl acetate/methanol mixture, Mp: 143-144° C.

The acetone filtrate of the salt formation was concentrated in vacuo. To the residue, 70 ml saturated sodium carbonate solution and 200 ml dichloromethane was added, after 15 minutes of stirring the phases were separated, the aqueous phase was extracted with dichloromethane (2×50 ml), the dichloromethane solution was dried over sodium sulfate and concentrated in vacuo. To the residual oil, 200 ml of 0.45M dry HCl in ethyl acetate was added and the volume of the solution was reduced by half with evaporation. The crystallized salt (S)-Ia.HCl was filtered after two hours of stirring, washed on the filter with ethyl acetate (3×5 ml) and dried at room temperature. The dry (S)-Ia.HCl mass is 6.5 g (78%), Mp: 138-140° C.; $[\alpha]_D$: +5.1 (c: 1, CHCl$_3$), ee 98.5%.

The isopropanol filtrate of the recrystallized diastereomeric salt was concentrated in vacuo and the residue (3.3 g) was processed analogously to the filtrate of the diastereomeric salt formation. The amount of the thus recovered (S,R)-Ia base was 1.2 g (17% based on half of the starting racemic base), ee: 17.0%. Similarly, by processing the filtrate of the diastereomeric salt formation and the ethyl acetate filtrate used in the hydrochloric salt formation of the resulting (S)-Ia base, nearly racemic composition of 1.4 g (20% based on half of the starting racemic base) (S,R)-Ia (ee: 21% and the regenerated bases can be recycled to the diastereomeric salt formation process) can be obtained.

2. Repeated Resolution of the Regenerated Ia Base

The regenerated (S,R)-Ia base (2.6 g, ee 19.6%) was dissolved in 26 ml of acetone and after addition of seed crystals, 4.44 g resolving agent II was added warmly. The mixture was allowed to cool under stirring, then the precipitated diastereomeric salt (R)-Ia.II was filtered, washed with a little acetone on the filter and dried (2.52 g). The salt was recrystallized from 55 ml isopropanol twice and the resulting pure 1.75 g (R)-Ia.II salt (ee: 99.4% yield 62%) can be used in the same manner as the diastereomeric salt from the original resolution.

The acetone filtrate of the diastereomeric salt formation was worked up in an analogous manner to the filtrate of the original resolution to yield 1.45 g of (S)-Ia.HCl salt (ee: 99.5%).

3. Resolution of the 3-ethylpiperidine-3-carboxylic acid ethyl ester (rac-Ib)

The rac-Ib.HCl salt (20.0 g, 90.3 mmol) was added to 200 ml of distilled water dissolved in sodium carbonate (28.7 g, 271.0 mmol) and the precipitating oil was dissolved in 100 ml of dichloromethane. The phases were separated, the aqueous solution was extracted with dichloromethane (3×50 mL), dried over sodium sulfate, and concentrated in vacuo. The residual colorless oil rac-Ib base (16.7 g) was dissolved in 167 ml of acetone and a small amount of (R)-Ib.II seed crystals (about 0.05 g) were added to the warm solution. Under stirring, diacetone-L-ketogulonic acid monohydrate (II, 26.4 g, 90.3 mmol) was added and initially heated to reflux to dilute the dense crystalline suspension then let the reaction mixture slowly cool down. The crystal suspension was stirred for 2 hours at room temperature, filtered on nutsche, washed with acetone (3×15 mL) and dried. The nutsche wet cake salt (about 27 g) was dried at room temperature (dry weight 18.1 g). The dry salt was dissolved in isopropanol (270 mL) hot, allowed to cool under stirring, stirred for two hours more at room temperature, filtered and washed with isopropanol on the filtrate. The recrystallized dry (R)-Ib.II salt was 15.4 g, 72%, (R)-Ib enantiomeric excess ee: 98.0% (HPLC), Mp: 186° C. (decomp.)

If necessary, the diastereomeric salt can be processed in the same way as the evaporation residue obtained from the filtrate of the salt formation (see the following paragraph). The enantiomeric purity of the so-produced (R)-Ib.HCl is >98.5%, Mp: 134-136° C., [α]$_D$: −4.5 (c: 1, CHCl$_3$).

The acetone filtrate of the diastereomeric salt formation was concentrated in vacuo. To the residue, 80 ml of a saturated sodium carbonate solution and 200 ml of dichloromethane was added, after 15 minutes of stirring, the phases were separated, the aqueous phase was extracted with dichloromethane (2×50 ml), the dichloromethane solution was dried over sodium sulfate and concentrated in vacuo. To the residual oil (10.4 g), 260 ml of 0.45M dry hydrochloric acid ethyl acetate was added and the volume of the solution was reduced by half with evaporation. The crystallized salt (S)-Ib.HCl was filtered after two hours of stirring, and washed with ethyl acetate (3×5 ml) on the filter and dried at room temperature. The dry (S)-Ib.HCl was 7.5 g (75%), Mp: 134-136° C.; [α]$_D$: +4.4 (c: 1, CHCl$_3$), ee 98.0%.

The isopropanol filtrate of the recrystallized diastereomeric salt was concentrated in vacuo and the residue (2.7 g) was processed analogously to the filtrate of the diastereomeric salt formation. The amount of the thus recovered (S,R)-Ib base was 1.04 g (12% based on half of the starting racemic base), ee: 20%. Similarly, by processing the filtrate of the diastereomeric salt formation and the ethyl acetate filtrate used in the hydrochloric salt formation of the resulting (S)-Ib base, nearly racemic composition of 2.88 g oil (34% based on half of the starting racemic base) (S,R)-Ib (ee: 4.5% and the regenerated bases can be recycled to the diastereomeric salt formation process) can be obtained.

4. Repeated Resolution of the Regenerated Ib Base:

The regenerated (S,R)-Ib base (3.9 g, ee 6.5%) was dissolved in 39 ml of acetone and after addition of seed crystals, 6.16 g of resolving agent II was added warmly. The mixture was allowed to cool under stirring, then the precipitated diastereomeric salt (R)-Ib.II was filtered, washed with a little acetone on the filter and dried (4.08 g). The salt was recrystallized from 66 ml isopropanol and the resulting pure 3.46 g (R)-Ib.II salt (ee: 99.2% yield 69%) is used in the same manner as the diastereomeric salt from the original resolution.

The acetone filtrate of the diastereomeric salt formation was worked up in an analogous manner to the filtrate of the original resolution to yield 1.50 g of (S)-Ib.HCl salt (76% ee: 98.4%).

5.1. Preparation of 3-isopropylpiperidine-3-carboxylic acid ethyl ester of (rac-Ic)

Under nitrogen atmosphere, a solution of 21 ml (21 mmol) of 1M lithium hexamethyldisilazane was added dropwise at (−78)° C. to (−65)° C. to a solution of 1-tert-butyl 3-ethylpiperidine-1,3-dicarboxylate (5 g, 19.4 mmol) in 60 ml abs. tetrahydrofuran and stirred for 20 minutes at this temperature. Then, 2.2 ml of 2-iodopropane was added dropwise and the cooling was stopped to allow to rise to room temperature, where it was stirred for an additional 18 hours. The reaction mixture was quenched with 50 ml of saturated ammonium chloride solution and with 50 ml of water, extracted with ethyl acetate. The combined organic phases were washed with water, dried over sodium sulfate, filtered and concentrated. The evaporation residue was purified by column chromatography using ethyl acetate-cyclohexane=1-4 eluents. To the thus prepared 1-tert-butyl 3-ethyl 3-isopropylpiperidine-1,3-dicarboxylate 10 ml of 2.5M hydrochloric acid ethyl acetate was added. After stirring at room temperature for 2 hours, the precipitated crystals of rac-Ic were filtered off, washed with diethyl ether and dried. Yield: 3.37 g 5.2. Resolution of 3-isopropylpiperidine-3-carboxylic acid ethyl ester of (rac-Ic)

The rac-Ic amine (19.5 g, 96.0 mmol) was dissolved in 157 ml of acetone and a small amount of (S)-Ic.II seed crystals (about 0.05 g) were added to the warm solution, the diacetone-L-ketogulonic acid monohydrate (II, 28.7 g, 96.6 mmol) was added while stirring and initially heated to reflux under stirring to dilute the dense crystalline suspension then let the reaction mixture slowly cool down. The crystal suspension was stirred overnight at room temperature, filtered on nutsche, washed with acetone (3×15 mL) and dried. The nutsche wet cake salt was dried at room temperature (dry weight 18.1 g, 77%). The dry salt was dissolved in isopropanol (185 mL) hot, allowed to cool under stirring, stirred for two hours more at room temperature, filtered and washed with isopropanol on the filtrate. The recrystallized dry (S)-Ic.II salt was 16.87 g, 70%, (S)-Ic enantiomeric excess ee: 98.4% (HPLC), Mp: 164-168° C. (decomp.)

If necessary, the diastereomeric salt can be processed in the same way as the evaporation residue obtained from the filtrate of the salt formation (see the following paragraph). The enantiomeric purity of the so-produced (S)-Ic.HCl is >98.5%, Mp: 152-154° C., [α]$_D$: −3.9 (c: 1, CHCl$_3$).

The acetone filtrate of the diastereomeric salt formation was concentrated in vacuo. To the residue, 35 ml of a saturated sodium carbonate solution (2 mol/L) and 100 ml of dichloromethane was added, after 15 minutes of stirring the phases were separated, the aqueous phase was extracted with dichloromethane (3×50 ml), the dichloromethane solution was dried over sodium sulfate and concentrated in vacuo. To the residual oil (12.0 g), 150 ml of 0.5M dry hydrochloric acid ethyl acetate was added and the volume of the solution was reduced to two-thirds with evaporation. The crystallized salt (R)-Ic.HCl was filtered after two hours of stirring, and washed with cold ethyl acetate (3×5 ml) on the filter and dried at room temperature. The dry (R)-Ic.HCl was 3.5 g (36%), Mp: 152-154° C.; [α]$_D$: +4.0 (c: 1, CHCl$_3$), ee 99.7%.

From the filtrate obtained after the extraction of the (R)-Ic.HCl salt, the (R)-Ic amine dissolved therein can be recovered by alkalizing and extraction and treated with more concentrated hydrochloric acid ethyl acetate to be able to obtain new hydrochloride salt generation or the regenerated base can be recycled to the resolution process.

The invention claimed is:

1. A process for the preparation of high enantiomerically pure optical isomers (R)-Ia, (R)-Ib, (R)-Ic, (S)-Ia, (S)-Ib, or (S)-Ic of the 3-alkylpiperidine-3-carboxylic acid ethyl ester of formula rac-I

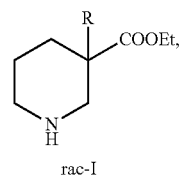

rac-I wherein R is methyl in (R)-Ia and (S)-Ia, R is ethyl in (R)-Ib and (S)-Ib, and R is isopropyl in (R)-Ic and (S)-Ic, the process comprising:

1) dissolving the amine of formula rac-I in a dipolar aprotic solvent at a temperature between 0° C. and 56° C. to form a mixture;
2) adding (−)-2,3:4,6-di-O-isopropylidene-2-keto-L-gulonic acid (diacetone-L-ketogulonic acid) resolving agent of formula II to the mixture,

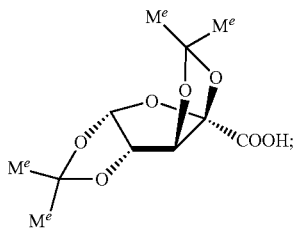

3) filtering the mixture to obtain crystalline (R)-Ia.II, (R)-Ib.II, or (S)-Ic.II salts, and a filtrate; and
4) obtaining high enantiomeric purity (R)-Ia, (R)-Ib, or (S)-Ic from the crystalline (R)-Ia.II, (R)-Ib.II, or (S)-Ic.II salts.

2. The process of claim 1, wherein the filtrate from step 3) is treated with hydrochloric acid to obtain crystalline (S)-Ia.HCl, (S)-Ib.HCl, or (R)-Ic.HCl salts.

3. The process of claim 2, further comprising obtaining high enantiomeric purity (S)-Ia, (S)-Ib, or (R)-Ic from the crystalline (S)-Ia.HCl, (S)-Ib.HCl, or (R)-Ic.HCl salts.

4. The process of claim 1, wherein seed crystals of (R)-Ia.II, (R)-Ib.II, or (S)-Ic.II salts are added to the mixture after step 2).

5. The process of claim 1, wherein the crystalline (R)-Ia.II, (R)-Ib.II, or (S)-Ic.II salts are recrystallized with isopropanol after step 3).

6. The process of claim 5, wherein the isomeric purity of the crystalline (R)-Ia.II, (R)-Ib.II, or (S)-Ic.II salts is increased following the recrystallization.

7. The process of claim 5, wherein the recrystallization results in a filtrate containing rac-Ia, rac-Ib, or rac-Ic.

8. The process of claim 7, wherein the rac-Ia, rac-Ib, or rac-Ic is used to prepare high enantiomerically pure optical isomers (R)-Ia, (R)-Ib, (R)-Ic, (S)-Ib, or (S)-Ic.

9. The process of claim 1, wherein the crystalline (R)-Ia.II, (R)-Ib.II, or (S)-Ic.II salts are treated with hydrochloric acid to obtain crystalline (R)-Ia.HCl, (R)-Ib.HCl, or (S)-Ic.HCl salts.

10. The process of claim 1, wherein the suitable organic solvent is acetone.

11. The process of claim 1, wherein the high enantiomerically pure optical isomers (R)-Ia, (R)-Ib, (R)-Ic, (S)-Ia, (S)-Ib, or (S)-Ic have an enantiomeric excess (ee) of 98% or greater.

12. The process of claim 1, wherein the temperature is between 20° C. and 56° C.

13. The process of claim 1, wherein the high enantiomerically pure optical isomers (R)-Ia, (R)-Ib, (R)-Ic, (S)-Ia, (S)-Ib, or (S)-Ic are obtained in a yield of 93% or greater.

14. The process of claim 1, wherein the resolving agent of formula II is used in an amount of 0.8 to 1.2 mole equivalents based on the amount of rac-I.

15. The process of claim 1, wherein the resolving agent of formula II is a monohydrate.

16. The process of claim 1, wherein the high enantiomeric purity (R)-Ia, (R)-Ib, or (S)-Ic are obtained from the crystalline (R)-Ia.II, (R)-Ib.II, or (S)-Ic.II salts using aqueous alkaline degradation.

* * * * *